United States Patent [19]

Miura et al.

[11] Patent Number: 5,137,909
[45] Date of Patent: Aug. 11, 1992

[54] INDOLE DERIVATIVE AND METHOD OF PRODUCTION THEREOF

[75] Inventors: Hidehiko Miura, Nogi; Naoki Harano, Okaya; Yasuo Takano, Kazo; Toshiro Mochizuki, Washimiya; Yoshinori Takahashi, deceased, late of Utsunomiya, by Saiko Takahashi, legal representative; Takashi Nagayama, Nogi, all of Japan

[73] Assignee: Kyorin Seiyaku Kabushiki Kaisha, Tokyo, Japan

[21] Appl. No.: 523,577

[22] Filed: May 14, 1990

[30] Foreign Application Priority Data

May 12, 1989 [JP] Japan .................. 1-119787

[51] Int. Cl.⁵ .................... A61K 31/40; C07D 201/30
[52] U.S. Cl. ................. 514/418; 514/229.8; 514/284; 514/285; 514/290; 514/339; 514/411; 544/89; 544/99; 544/101; 546/62; 546/71; 546/94; 546/272; 548/150; 548/427; 548/432; 548/486
[58] Field of Search ............... 514/418; 548/484, 432, 548/486

[56] References Cited

U.S. PATENT DOCUMENTS

| 3,803,319 | 4/1974 | Musajo | 514/418 |
| 4,059,583 | 11/1977 | McComsey | 548/486 |
| 4,654,360 | 3/1987 | Greenhouse et al. | 548/484 |
| 4,882,329 | 11/1989 | Lerch | 514/418 |
| 4,994,474 | 2/1991 | Gubin | 548/484 |

FOREIGN PATENT DOCUMENTS

| 0397210 | 11/1990 | European Pat. Off. | 548/486 |
| 2054462 | 4/1971 | France | 548/432 |
| 0027861 | 11/1968 | Japan | 548/484 |

OTHER PUBLICATIONS

Ishizuka, Jour. Chem. Soc. Perkin Trans. 1, pp. 813-826 (1990).
Lednicer et al., Jour. Hetero. Chem., vol. 8, pp. 903-910 (1971).
Ishizuka et al., in 9th Int'l Congress of Het. Chem., Hokkaido Univ., 1983, p. 397.

Primary Examiner—Donald G. Daus
Attorney, Agent, or Firm—McAulay Fisher Nissen Goldberg & Kiel

[57] ABSTRACT

An indole derivative represented by the general formula (I)

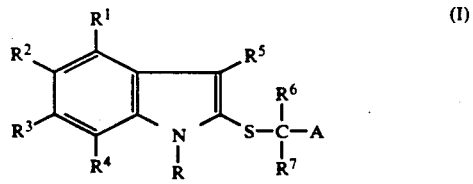

wherein
R is hydrogen, lower alkyl having 1 to 6 carbons, carboxymethyl, or substituted or unsubstituted aralkyl;
$R^1$, $R^2$, $R^3$, and $R^4$ may be the same with or different from each other and are hydrogen, halogen, lower alkyl having 1 to 6 carbons, lower alkoxy having 1 to 6 carbons, acyl, substituted or unsubstituted amino, nitro, hydroxy, acyloxy, substituted or unsubstituted aralkyl, substituted or unsubstituted aryloxy, or substituted or unsubstituted aralkyloxy, or a combination of $R^2$ and $R^3$ may be methylenedioxy;
$R^5$ is hydrogen, lower alkyl having 1 to 6 carbons, or substituted or unsubstituted aralkyl; R and $R^4$, or $R^1$ and $R^5$ may form together a six-membered ring constituted of methylene chains which may contain a heteroatom;
$R^6$ and $R^7$ may be the same with or different from each other and are hydrogen, lower alkyl having 1 to 6 carbons, or substituted or unsubstituted aryl or a five- or six-membered heterocyclic ring;
A is —COOR⁸ (wherein $R^8$ is hydrogen, lower alkyl having 1 to 6 carbons, substituted or unsubstituted aralkyl, or substituted or unsubstituted aryl), or —CH₂OR⁹ (wherein $R^9$ is hydrogen, lower alkyl having 1 to 6 carbons, lower alkenyl having 2 to 6 carbons, acyl or substituted or substituted aralkyl);
and the method of producing the same, which comprises reacting, in the presence of a base, useful for hyperlipidemia and arteriosclerosis, is disclosed.

2 Claims, No Drawings

INDOLE DERIVATIVE AND METHOD OF PRODUCTION THEREOF

BACKGROUND OF THE INVENTION

1. Field of the Invention

The present invention relates to an indole derivative which is highly useful for therapy and prophylaxis of hyperlipidemia and arteriosclerosis. The present invention also relates to a method of production of the indole derivative and a lipid lowering agent containing the indole derivative as an active ingredient.

2. Description of the Related Art

Hyperlipidemia which gives an abnormally high level of serum lipid has been considered to be a clinical disease by itself and to be a cause of arteriosclerosis. For amelioration of abnormalities in lipid metabolism, medicines, such as, nicotinic acid or derivatives thereof, clofibrate, and phenyl alkyl ethers having a partial structure of the clofibrate are frequently used. In recent years, melinamide: a linoleamide derivative, probucol: a bisphenol derivative, colestyramine: an ion exchange resin and the like have come to be used for clinical therapy. Furthermore, tazasubrate which has a structure analogous to that of the compound of the present invention is known (Merck Patent G.m.b.H.: Japanese Patent Kokai Sho 56-92881, corresponding to European Patent Application EP 30632 and U.S. Pat. No. 4,294,839). For the present purpose, however, a compound having an indole skeleton like the one of the present invention is not known.

A compound having thioacetic acid group at the 2-position of an indole ring is described in J. Heterocycl. Chem., 8, 903 (1971). This compound, however, has a phenyl group at the 3-position in the structure thereof, which is completely different from the one of the present invention. Moreover, nothing is described regarding the pharmacological activity of the compound.

Recently, low density lipoprotein-cholesterol (LDL-Ch) has been indicated as an arteriosclrosis factor, and high density lipoprotein-cholesterol (HDL-Ch) has been indicated as antiarteriosclerosis factor. That is, the amelioration of the arteriosclerotic index (AI) represented by the ratio of an LDL-Ch value to the a HDL-Ch value in serum by lowering the LDL-Ch value and raising the HDL-Ch value is considered to be important, rather than simply lowering the level of the total cholesterols, triglycerides, and the like. Nevertheless, the medicines used for clinical therapy thereof at present are not satisfactory. Thus the medicine is desired which is effective in ameliorating abnormal lipid metabolism and yet is highly safe.

SUMMARY OF THE INVENTION

The present invention provides a a medicine for the therapy and prophylaxis of hyperlipidemia and arteriosclerosis.

More particularly, the present invention provides an indole derivative represented by the general formula (I):

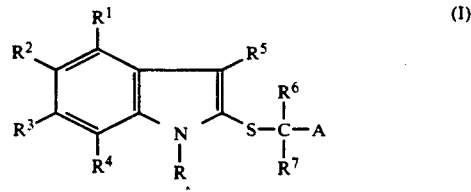

wherein

R is hydrogen, lower alkyl having 1 to 6 carbons, carboxymethyl, or substituted or unsubstituted aralkyl; $R^1$, $R^2$ $R^3$, and $R^4$ may be the same with or different from each other and are hydrogen, halogen, lower alkyl having 1 to 6 carbons, lower alkoxy having 1 to 6 carbons, acyl, substituted or unsubstituted amino, nitro, hydroxy, acyloxy, substituted or unsubstituted aralkyl, substituted or unsubstituted aryloxy, or substituted or unsubstituted aralkyloxy, or a combination of $R^2$ and $R^3$ may be methylenedioxy;

$R^5$ is hydrogen, lower alkyl having 1 to 6 carbons, or substituted or unsubstituted aralkyl;

R and $R^4$, or $R^1$ and $R^5$ may form together a six-membered ring constituted of methylene chains which may contain a heteroatom;

$R^6$ and $R^7$ may be the same with or different from each other and are hydrogen, lower alkyl having 1 to 6 carbons, or substituted or unsubstituted aryl or a five- or six-membered heterocyclic ring;

A is $-COOR^8$ wherein $R^8$ is hydrogen, lower alkyl having 1 to 6 carbons, substituted or unsubstituted aralkyl, or substituted or unsubstituted aryl, or $CH_2OR^9$ wherein $R^9$ is hydrogen, lower alkyl having 1 to 6 carbons, lower alkenyl having 2 to 6 carbons, acyl or substituted or unsubstituted aralkyl;

and the pharmaceutically acceptable salts and the hydrates thereof.

DETAILED DESCRIPTION OF THE INVENTION

As the results of comprehensive study on medicines for therapy and prophylaxis of hyperlipidemia and arteriosclerosis, it has now been found that the compound represented by the general formula (I) above has a strong effect of ameliorating the abnormality of lipid metabolism with high safety.

In the above general formula (I), the lower alkyl includes straight or branched alkyl group having 1 to 6 carbons, among which methyl, ethyl, propyl, isoamyl, and butyl are preferable. The substituted or unsubstituted aralkyl includes benzyl, phenylethyl, phenylpropyl, and the like which may be substituted by one or more halogens, lower alkyl groups, lower alkoxy groups and the like on the phenyl ring, among which are benzyl, p-chlorobenzyl, 3,4-dimethoxybenzyl, are preferable and The preferable halogens are fluorine, chlorine and bromine. The acyl includes lower alkylcarbonyl, arylcarbonyl, aralkylcarbonyl, and the like, among which acetyl, benzoyl, and crotonyl are preferable. The acyloxy includes lower alkylcarbonyloxy, arylcarbonyloxy, aralkylcarbonyloxy, and the like, among which are acetyloxy, p-chlorobenzoyloxy, 3-pyridinecarbonyloxy are preferred. The alkoxy includes straight or branched alkoxy groups having an alkyl portion of 1 to 6 carbons, among which are methoxy, ethoxy, isopropoxy, and n-hexyloxy are preferred. The substituted or unsubstituted aryl includes phenyl and naphthyl which may be substituted by one or more halogens, lower alkyl groups, lower alkoxy groups, or the like, among which phenyl, p-chlorophenyl, p-methylphenyl, and 2,3-dimethylphenyl are preferred. The substituted or unsubstituted aryloxy includes phenoxy, naphthyloxy, and the like which may be substituted by one or more halogens, lower alkyl groups, lower alkoxy groups. or the like. The substituted or unsubstituted aralkyloxy includes benzyloxy, phenylethoxy, phenylpropoxy, and the like which may be substituted on the phenyl ring by one or more halogens, lower alkyl groups, lower alkoxy groups or the like, among which benzyloxy, m-fluorobenzyloxy, and p-methylbenzyloxy are preferred. R and $R^4$, or $R^1$ and $R^5$ taken together may form a six-membered ring made up of methylene chains which may include a heteroatom, such as oxygen, nitrogen, and sulfur. The five- or six-membered heterocylcic ring of $R^6$ or $R^7$ includes pyridyl, pyrimidyl, imidazolyl, thiazolyl, and the like, among which 2- or 3-pyridyl, 3-pyrazolyl, and 2-thiazolyl rings are preferable.

The compound represented by the general formula (I) can be produced through the routes shown below.

(1) The compound of the general formula (I) in which A is —$COOR^8$ (wherein $R^8$ is hydrogen, lower alkyl having 1 to 6 carbons, substituted or unsubstituted aralkyl, or substituted or unsubstituted aryl) can be produced by reacting a compound represented by the general formula (III) with a compound represented by the general formula (IV), each shown below in the presence of a base, and if necessary hydrolyzing it. More specifically, the reaction may be conducted in the presence of an alkali metal hydroxide such as sodium hydroxide, potassium hydroxide and the like, an alkali metal carbonate such as sodium carbonate, potassium carbonate, etc., an organic base such as triethylamine, 1,8-diazabicyclo[5,4,0]-7-undecene, etc, or the like as the base, in a suitable solvent such as dimethylformamide, dimethyl sulfoxide, an alcohol, and the like within a temperature range of from 0° to 150° C., preferably from 20° to 100° C. Subsequently, if necessary, the carboxylic ester is hydrolyzed to a corresponding carboxylic acid. This reaction may be carried out in the presence of an alkali such as sodium hydroxide, potassium hydroxide, and the like in a suitable solvent such as water, an alcohol, dimethylformamide or a mixture thereof, and the like within the temperature range of from 0° to 150° C., preferably from 20° to 100° C.

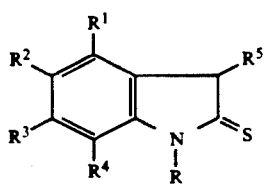

(III)

wherein R, $R^1$, $R^2$, $R^3$, $R^4$, and $R^5$ are as defined above:

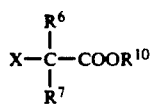

(IV)

wherein $R^6$ and $R^7$ are as defined above, X is halogen and $R^{10}$ is lower alkyl having 1 to 6 carbons, substituted or unsubstituted aralkyl, or substituted or unsubstituted aryl.

(2) The compound of the general formula (I) in which A is —COOH can be produced by reacting a compound of the general formula (VI) with a compound of the general formula (IV) in the presence of a base to obtain a compound of general formula (VII) below, and subsequently opening the ring. More specifically, the reaction may be conducted in the presence of an alkali metal hydroxide such as sodium hydroxide, potassium hydroxide, and the like, an alkali metal carbonate such as sodium carbonate, potassium carbonate, and the like, an organic base such as triethylamine, 1,8-diazabicyclo[5,4,0]-7-undecene, and the like, or the like as the base, in a suitable solvent such as dimethylformamide, dimethyl sulfoxide, an alcohol, and the like within the temperature range of from 0° to 150° C., preferably from 20° to 100° C. Subsequently, the resulting compound of the general formula (VII) is subjected to ring opening to convert it to the corresponding carboxylic acid form. This reaction may be carried out in the presence of an alkali such as sodium hydroxide, potassium hydroxide and the like in a suitable solvent such as water, an alcohol, dimethylformamide, and the like or a mixture thereof within the temperature range of from to 150° C., preferably from 20° to 100° C.

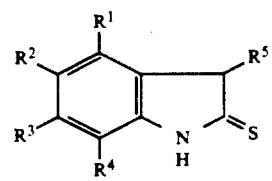

(VI)

wherein $R^1$, $R^2$, $R^3$, $R^4$, and $R^5$ are as defined above;

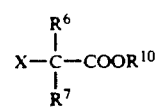

(IV)

wherein $R^6$ and $R^7$ are as defined above, X is halogen, and $R^{10}$ is lower alkyl having 1 to 6 carbons, substituted or unsubstituted aralkyl, or substituted or unsubstituted aryl,

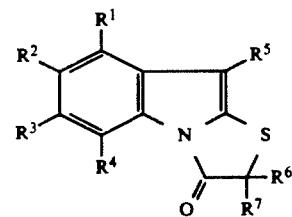

(VII)

wherein $R^1$, $R^2$, $R^3$, $R^4$, $R^5$, $R^6$, and $R^7$ are as defined above.

(3) The compound of the general formula (I) in which A is —$COOR^{10}$ (wherein $R^{10}$ is lower alkyl having 1 to 6 carbons or substituted or unsubstituted aralkyl) can be produced by reacting a compound of general formula (IX) with a compound of the general formula (X) in the presence of diethyl azodicarboxylate and triphenylphosphine. More specifically, the reaction may be conducted in the presence of diethyl azodicarboxylate and triphenylphosphine in an appropriate solvent such as ether, tetrahydrofuran, benzene and the preferably from −20° to 50° C.

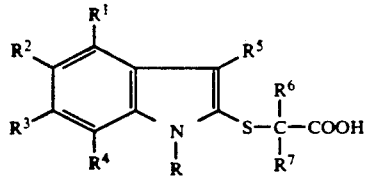

(IX)

wherein R, $R^1$, $R^2$, $R^3$, $R^4$, $R^5$, $R^6$, and $R^7$ are as defined above.

(X)

wherein $R^{10}$ is as defined above.

(4) The compound of the general formula (I) in which A is —CH$_2$OH can be produced by reducing a compound of the general formula (II). More specifically, the reaction may be conducted in the presence of a reducing agent such as lithium aluminum hydride, sodium cyanoboro-hydride, lithium borohydride, and the like in an appropriate solvent such as ether, tetrahydrofuran, toluene, and the like within the temperature range of from 0° to 200° C., preferably from 20° to 150° C.

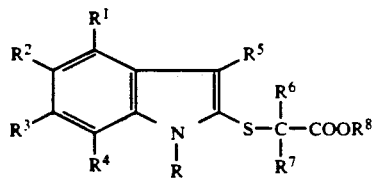

(II)

wherein R, $R^1$, $R^2$, $R^3$, $R^4$, $R^5$, $R^6$, $R^7$, and $R^8$ are as defined above.

(5) The compound of the general formula (I) in which A is —CH$_2$OH can be produced by reacting in such a manner that a compound of the general formula (IX) with an α-halo-ester to form a mixed acid anhydride and reducing the product. More specifically, the reaction may be conducted in the presence of a reducing agent such as sodium borohydride and the like in an appropriate solvent such as tetrahydrofuran, ethanol, water, dioxane, and the like within the temperature range of from 0° to 50° C., preferably from 10° to 30° C.

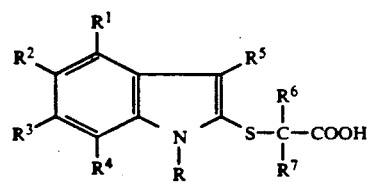

(IX)

wherein R, $R^1$, $R^2$, $R^3$, $R^4$, $R^5$, $R^6$, and $R^7$ are as defined above.

(6) The compound of the general formula (I) in which A is —CH$_2$OR$^{11}$ (wherein $R^{11}$ is lower alkyl having 1 to 6 carbons, lower alkenyl having 2 to 6 carbons, acyl, or substituted or unsubstituted aralkyl) can be produced by reacting a compound of the general formula (XI) and a compound of the general formula (XIII). More specifically, the reaction may be conducted in a solvent such as dioxane, dimethylformamide, tetrahydrofuran, benzene and the like within the temperature range of from 0° to 200° C., preferably from 20° to 150° C.

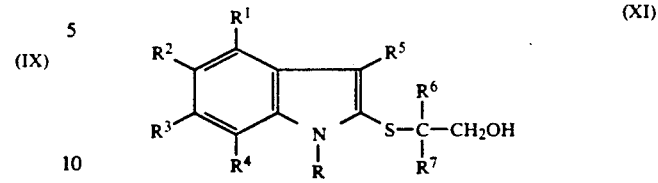

(XI)

wherein R, $R^1$, $R^2$, $R^3$, $R^4$, $R^5$, $R^6$, and R are as defined above.

(XIII)

wherein $R^{11}$ is a lower alkyl having 1 to 6 carbon, acyl, lower alkenyl having 2 to 6 carbons, or substituted or unsubstituted aralkyl, and Y is halogen.

(7) The compound of the general formula (I) in which R is $R^{12}$ (wherein $R^{12}$ is lower alkyl having 1 to 6 carbons, carboxymethyl, or substituted or unsubstituted aralkyl) can be produced by reacting a compound of the general formula (XV) and a compound of the general formula (XVI). More specifically, the reaction may be conducted in a solvent such as dimethylformamide, tetrahydrofuran, benzene and the like within the temperature range of from 0° to 100° C., preferably from 10° to 50° C.

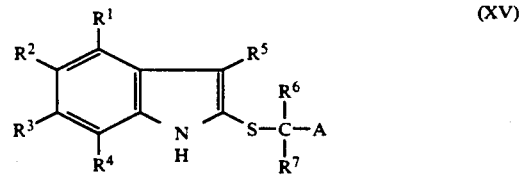

(XV)

wherein $R^1$, $R^2$, $R^3$, $R^4$, $R^5$, $R^6$, $R^7$, and A are as defined above.

(XVI)

wherein $R^{12}$ is as defined above, and Y is halogen.

The compounds represented by the general formula (I) includes optical isomers resulting from an asymmetric carbon these isomers and mixtures thereof are represented by a single formula for convenience, which does not limit the present invention.

The compounds of the general formula (I) in which A is —COOH may be converted to the salts thereof according to a conventional method, if necessary. The salts includes those of sodium, potassium, magnesium, calcium, aluminum, cerium, chromium, cobalt, copper, iron, zinc, platinum, silver and the like.

The following examples illustrate the present invention:

EXAMPLE 1

Ethyl 2-(1H-indol-2-yl)thio-2-phenylpropionate

Into a solution of 1,3-dihydroindol-2-thione (19.7 g) and ethyl 2-bromo-2-phenylpropionate (33.9 g) indimethylformamide (DMF, 200 ml), an aqueous 2 N sodium hydroxide solution (66 ml) was added dropwise under ice cooling, and the mixture was stirred at room temperature for 2 hours. The reaction mixture was diluted with water, and was extracted with ethyl acetate. The organic layer was washed with water, and then with saturated aqueous sodium chloride solution, and was dried over anhydrous sodium sulfate. The solvent was evaporated under reduced pressure. n-Hexane was added to the evaporation residue to cause crystallization. The resulting crystalline matter was recrystallized from ethyl acetate/n-hexane to give 30.3 g (yield: 71%) of product compound as a pale yellow crystal form. The melting point was 97°–99° C.

Elemental analysis (as $C_{19}H_{19}NO_2S$): Calcd. (%); C: 70.13, H: 5.88, N: 4.30; Found (%); C: 70.38, H: 5.89, N: 4.26

EXAMPLES 2 TO 38

The compounds shown in Table 1 were synthesized in a similar manner as in Example 1.

TABLE 1
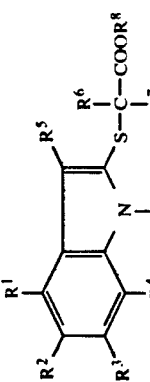
| Example | R | $R^1$ | $R^2$ | $R^3$ | $R^4$ | $R^5$ | $R^6$ | $R^7$ | $R^8$ | Melting Point (°C.) |
|---|---|---|---|---|---|---|---|---|---|---|
| 2 | H | H | H | H | H | H | H | H | $C_2H_5$ | 54-59 |
| 3 | H | H | H | H | H | H | H | $CH_3$ | $C_2H_5$ | 62-63 |
| 4 | H | H | H | H | H | H | H | $n-C_4H_9$ | $C_2H_5$ | Oily |
| 5 | H | H | H | H | H | H | $CH_3$ | $CH_3$ | $C_2H_5$ | — |
| 6 | H | H | H | H | H | H | $CH_3$ | $C_2H_5$ | $C_2H_5$ | 71-73 |
| 7 | H | H | H | H | H | H | $C_2H_5$ | $C_2H_5$ | $C_2H_5$ | 82-86 |
| 8 | H | H | H | H | H | H | H | $C_6H_5$ | $C_2H_5$ | 113-114 |
| 9 | H | H | H | H | H | H | $C_2H_5$ | $C_6H_5$ | $C_2H_5$ | 98.5-99.5 |
| 10 | H | H | H | H | H | H | $n-C_3H_7$ | $C_6H_5$ | $C_2H_5$ | — |
| 11 | H | H | H | H | H | H | $(CH_3)_2CH(CH_2)_2$ | $C_6H_5$ | $C_2H_5$ | Oily |
| 12 | H | H | H | H | H | H | $C_6H_5$ | $C_6H_5$ | $C_2H_5$ | Oily |
| 13 | $CH_3$ | H | H | H | H | H | $CH_3$ | $C_6H_5$ | $C_2H_5$ | — |

TABLE 1-continued

| No. | R | R¹ | R² | R³ | R⁴ | R⁵ | R⁶ | R⁷ | R⁸ | m.p. (°C) |
|---|---|---|---|---|---|---|---|---|---|---|
| 14 | CH$_3$ | H | H | H | H | H | n-C$_3$H$_7$ | C$_6$H$_5$ | C$_2$H$_5$ | 71–73 |
| 15 | CH$_2$C$_6$H$_5$ | H | H | H | H | H | CH$_3$ | C$_6$H$_5$ | C$_2$H$_5$ | Oily |
| 16 | 4-Cl-C$_6$H$_4$-CH$_2$ | H | H | H | H | H | CH$_3$ | C$_6$H$_5$ | C$_2$H$_5$ | — |
| 17 | H | F | H | H | H | H | C$_2$H$_5$ | C$_6$H$_5$ | C$_2$H$_5$ | 120–121 |
| 18 | H | Cl | H | H | H | H | CH$_3$ | C$_6$H$_5$ | C$_2$H$_5$ | 104–106 |
| 19 | H | CH$_3$ | H | H | H | H | CH$_3$ | C$_6$H$_5$ | C$_2$H$_5$ | 113–115 |
| 20 | H | CH$_3$O | H | F | H | H | CH$_3$ | C$_6$H$_5$ | C$_2$H$_5$ | 133–135 |

TABLE 1-continued
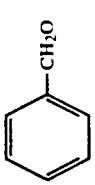
| No | R¹ | R² | R³ | R⁴ | R | R⁵ | R⁶ | R⁷ | R⁸ | m.p. |
|---|---|---|---|---|---|---|---|---|---|---|
| 21 | H | H | H | H | -CH₂-C₆H₅ | H | CH₃ |  | C₂H₅ | Oily |
| 22 | H | H | H | H | CH₃COO | H | CH₃ |  | C₂H₅ | Oily |
| 23 | H | H | H | H | H | CH₃ | CH₃ |  | C₂H₅ | Oily |
| 24 | H | H | H | H | H | -CH₂-C₆H₅ | CH₃ |  | C₂H₅ | Oily |
| 25 | H | H | H | H | H | -CH₂-C₆H₃(OCH₃)₂ | CH₃ |  | C₂H₅ | Oily |
| 26 | H | CH₃ | CH₃ | H | H | H | CH₃ |  | C₂H₅ | 97-98 |
| 27 | H | CH₃ | H | CH₃ | H | H | CH₃ |  | C₂H₅ | Oily |

TABLE 1-continued

| | | | | | | | | | | | |
|---|---|---|---|---|---|---|---|---|---|---|---|
| 28 | H | CH₃O | H | H | H | H | ⌬ | CH₃ | C₂H₅ | | Oily |
| 29 | H | CH₃O | H | Cl | H | H | ⌬ | C₂H₅ | C₂H₅ | | — |
| 30 | H | CH₃O | CH₃O | H | H | H | ⌬ | CH₃ | C₂H₅ | | — |
| 31 | H | CH₃O | —OCH₂O— | | H | H | ⌬ | CH₃ | C₂H₅ | | 126–127 |
| 32 | CH₃ | H | H | H | H | H | pyridyl | CH₃ | C₂H₅ | | Oily |
| 33 | H | H | H | H | H | H | ⌬ | C₂H₅ | CH₃ | | 121–123 |

| Example | R | R⁴ | R¹ | R² | R³ | R⁵ | R⁶ | R⁷ | R⁸ | Melting Point (°C) |
|---|---|---|---|---|---|---|---|---|---|---|
| 34 | —CH₂CH₂O— | CH₃O | H | H | H | H | H | CH₃ | CH₃ | C₂H₅ | Oily |

Structure:

R¹–R⁴ on benzene ring fused to pyrrole (N–R), with R⁵ at C-3 and at C-2: —S—C(R⁶)(R⁷)—COOR⁸

TABLE 1-continued

[Structure: substituted phenyl ring with R¹, R², R³, R⁴ substituents, connected to N(R) group, with C=C bearing R⁵ and S-C(R⁶)(R⁷)-COOR⁸]

| Example | R | R¹ | R² | R³ | R⁴ | R⁵ | R⁶ | R⁷ | R⁸ | Melting Point (°C.) |
|---|---|---|---|---|---|---|---|---|---|---|
| 35 | H | —CH₂CH₂O— | | H | Cl | H | CH₃ | (phenyl) | C₂H₅ | Oily |
| 36 | H | —CH₂CH₂O— | | H | H | H | CH₃ | (phenyl) | C₂H₅ | Oily |
| 37 | H | —CH₂CH₂CH₂— | | H | H | H | CH₃ | (phenyl) | C₂H₅ | 75–77 |
| 38 | | —CH₂CH₂CH₂— | | | | | —CH₃ | (phenyl) | C₂H₅ | 125–126 |

EXAMPLE 39

2-(1H-indol-02-yl)thio-2-phenylpropionic acid

To a suspension (57.6 ml) of ethyl 2-(1H-indol-2-yl)thio-2-phenylpropionate (2.88 g) in ethanol, there was added an aqueous solution (12 ml) of potassium hydroxide (1.5 g). The mixture was heated and refluxed for 1 hour. The reaction mixture was allowed to cool. The organic solvent was evaporated off under a reduced pressure. Water was added to the residual matter, and the mixture was extracted with ethyl acetate. The organic layer was washed with water and a saturated aqueous sodium chloride solution, and was dried over anhydrous sodium sulfate. The solvent was evaporated under reduced pressure. The residue was recrystallized from benzene to give 2.12 g (yield: 73.1%) of the product compound as colorless prisms. The melting point was 165°–167° C.

Elemental analysis (as $C_{17}H_{15}NO_2S$): Calcd. (%); C: 68.66, H: 5.08, N: 4.71; Found (%); C: 68.96, H: 5.11, N: 4.76

EXAMPLES 40 TO 69

The compounds shown in Table 2 were synthesized in a similar manner as in Example 39.

TABLE 2

$$\text{[structure: benzene ring with R}^1\text{, R}^2\text{, R}^3\text{, R}^4 \text{ substituents, connected to N-R, C=C with R}^5\text{, and S-C(R}^6\text{)(R}^7\text{)-COOH]}$$

| Example | R | R¹ | R² | R³ | R⁴ | R⁵ | R⁶ | R⁷ | Melting Point (°C.) | Elemental Analysis (%) Calcd./Found C | H | N |
|---|---|---|---|---|---|---|---|---|---|---|---|---|
| 40 | CH₃ | H | H | H | H | H | CH₃ | [phenyl] | 161–163 | 69.43 / 69.23 | 5.50 / 5.62 | 4.50 / 4.45 |
| 41 | H | H | H | H | H | H | H | [phenyl] | 143–144 | 67.82 / 68.04 | 4.62 / 4.59 | 4.94 / 4.89 |
| 42 | H | H | H | H | H | H | H | H | 99–101 | 57.95 / 58.21 | 4.38 / 4.37 | 6.76 / 6.68 |
| 43 | H | H | H | H | H | H | CH₃ | CH₃ | 118–119 | 61.25 / 61.46 | 5.57 / 5.56 | 5.95 / 5.91 |
| 44 | H | H | Cl | H | H | H | CH₃ | [phenyl] | 156–159 | 61.54 / 61.58 | 4.25 / 4.19 | 4.22 / 4.17 |
| 45 | H | H | —OCH₂O— | | H | H | CH₃ | [phenyl] | 162–164 | 63.33 / 63.61 | 4.43 / 4.40 | 4.10 / 4.03 |
| 46 | H | H | H | H | H | H | CH₃ | C₂H₅ | 84–86 | 62.62 / 62.72 | 6.06 / 6.08 | 5.62 / 5.53 |
| 47 | H | H | H | H | H | H | C₂H₅ | C₂H₅ | 122–124 | 63.85 / 63.85 | 6.51 / 6.58 | 5.32 / 5.28 |

TABLE 2-continued

Structure:

R¹, R², R³, R⁴ on benzene ring; N–R; vinyl C with R⁵; S–C(R⁶)(R⁷)–COOH

| No. | R¹ | R² | R³ | R⁴ | R | R⁵ | R⁶ | R⁷ | mp (°C) | Elemental Analysis C, H, N (Calc/Found) |
|---|---|---|---|---|---|---|---|---|---|---|
| 48 | H | H | H | H | H | C₂H₅ |  | phenyl | 155–157 | 69.43 5.50 4.50 / 69.45 5.47 4.47 |
| 49 | H | H | H | H | H | 4-Cl-C₆H₄-CH₂ |  | phenyl | 156–158 | 73.51 4.77 3.90 / 73.85 4.78 3.75 |
| 50 | H | H | H | H | H | CH₃ | C₆H₅-CH₂ | phenyl | 149–150 | 68.32 4.78 3.32 / 68.55 4.81 3.25 |
| 51 | H | H | H | H | H | CH₃ |  | phenyl | 176–177 | 74.39 5.46 3.61 / 74.33 5.41 3.51 |
| 52 | H | H | H | H | CH₃ | CH₃ |  | phenyl | 165–166 | 69.43 5.50 4.50 / 69.33 5.45 4.39 |
| 53 | H | CH₃ | H | H | H | CH₃ |  | phenyl | 171–173.5 | 69.43 5.50 4.50 / 69.30 5.50 4.48 |
| 54 | CH₃O | CH₃O | CH₃O | H | H | CH₃ |  | phenyl | 156–158 | 62.00 5.46 3.62 / 62.04 5.42 3.57 |

TABLE 2-continued

| No. | R¹ | R² | R³ | R⁴ | R | R⁵ | Ar | mp (°C) | Analysis Calcd / Found |
|---|---|---|---|---|---|---|---|---|---|
| 55 | H | CH₃O | H | CH₃O | H | H | C₂H₅ | phenyl | 146–148 | 64.67 5.70 3.77 / 64.60 5.70 3.67 |
| 56 | H | CH₃O | CH₃O | H | H | H | CH₃ | phenyl | Amorphous | 62.59 5.47 3.84*1 / 62.63 5.63 3.54 |
| 57 | H | H | H | H | CH₂-C₆H₅ | H | CH₃ | phenyl | 149–151 | 74.39 5.46 3.61 / 74.48 5.46 3.51 |
| 58 | CH₂COOH | H | H | H | H | H | CH₃ | phenyl | 192–196 | 64.21 4.82 3.94 / 64.35 4.83 3.89 |
| 59 | H | H | H | H | CH₂O-C₆H₅ | H | CH₃ | phenyl | 159–160 | 72.22 5.34 3.34*2 / 72.17 5.35 3.39 |
| 60 | H | CH₃ | CH₃ | H | H | H | CH₃ | phenyl | 112–114 | 70.13 5.88 4.30 / 70.37 5.92 4.26 |
| 61 | H | CH₃ | H | CH₃ | H | H | CH₃ | phenyl | 97–98 | 71.36 6.56 3.96 / 71.62 6.61 3.93 |

Structural formula header:

$$\text{Ar-ring with } R^1, R^2, R^3, R^4 \text{ substituents; } N-R; =C(R^5)-S-C(R^6)(R^7)-COOH$$

TABLE 2-continued

| Example | R | R⁴ | R¹ | R² | R³ | R⁵ | R⁶ | R⁷ | Melting Point (°C) | Elemental Analysis (%) Calcd./Found | | |
|---|---|---|---|---|---|---|---|---|---|---|---|---|
| | | | | | | | | | | C | H | N |
| 62 | H | H | H | H | H | H | CH₃ | 2,4-dimethylphenyl | 93–95 | 71.01 / 70.83 | 5.75 / 5.99 | 2.96*³ / 2.75 |
| 63 | CH₃ | H | H | H | H | H | CH₃ | 3-pyridyl | 219 (Decomposition, K salt) | 57.66 / 57.37 | 4.38 / 4.22 | 7.91*⁴ / 7.85 |
| 64 | H | H | CH₃O | H | H | H | CH₃ | phenyl | 160–162 | 66.03 / 65.90 | 5.23 / 5.20 | 4.28 / 4.21 |
| 65 | —CH₂CH₂O— | H | H | H | H | H | CH₃ | phenyl | 166 | 61.04 / 61.15 | 4.31 / 4.23 | 3.75 / 3.74 |
| 66 | —CH₂CH₂O— | H | H | Cl | H | H | CH₃ | CH₃ | 181–182 | 53.93 / 54.04 | 4.53 / 4.48 | 4.49 / 4.52 |
| 67 | —CH₂CH₂O— | H | H | H | H | H | CH₃ | phenyl | 161–163 | 67.24 / 67.71 | 5.05 / 5.11 | 4.13 / 4.03 |

TABLE 2-continued

[Structure: phenyl ring with R¹, R², R³, R⁴ substituents, N-R group, and vinyl group with R⁵, R⁶, S-C(R⁷)-COOH]

| Example | R | R¹ | R² | R³ | R⁴ | R⁵ | R⁶ | R⁷ | Melting Point (°C.) |
|---|---|---|---|---|---|---|---|---|---|
| 68 | —CH₂CH₂CH₂— | | H | H | H | H | | CH₃ | Ph | 151-153 |
| 69 | H | —CH₂CH₂CH₂— | H | H | H | | CH₃ | Ph | 161-162 |

| Example | Elemental Analysis (%) Calcd. Found | | |
|---|---|---|---|
| | C | H | N |
| 68 | 71.19 | 5.68 | 4.15 |
| | 71.03 | 5.61 | 4.01 |
| 69 | 71.19 | 5.68 | 4.15 |
| | 71.39 | 5.72 | 4.05 |

*¹Calculated as 4/5 hydrate
*²Calculated as 1/3 benzene
*³Calculated as 1/3 benzene
*⁴Calculated as 1/5 hydrate

EXAMPLE 70

2-(5-hydroxy-1H-indol-2-yl)thio-2-phenylpropionic acid (i) To a solution (13 ml) of 1,3-dihydro-5-hydroxyindol-2-thione (1.26 g) and ethyl 2-bromo-2-phenylpropionate (1.88 g) in DMF, an aqueous 2N sodium hydroxide solution (7.3 ml) was added dropwise under ice cooling, and the mixture was stirred at room temperature for 3 hours. The reaction mixture was diluted with water, made acidic by adding 6N hydrochloric acid, and extracted with ethyl acetate. The organic layer was washed with water, and a saturated aqueous sodium chloride solution, and was dried over sodium sulfate. The solvent was evaporated under reduced pressure, and the residue was purified by silica gel column chromatography (diluting solvent: methylene chloride) to give 1.77 g (yield: 81/9 %) of 7-hydroxy-2-methyl-2-phenylthiazolo[3,2-a]indol-3(2H)-one.

(ii) To the 7-hydroxy-2-methyl-2-phenylthiazolo[3,2-a]indol-3(2H)-one (3.65 g), a 2N sodium hydroxide solution (70 ml) was added, and the mixture was heated and refluxed for 30 minutes. The reaction mixture was allowed to cool, and was washed with ethyl acetate. The water layer was acidified with 6N hydrochloric acid, and extracted with ethyl acetate. The organic layer was washed with water, and a saturated aqueous sodium chloride solution, and was dried over anhydrous sodium sulfate. The solvent was evaporated under reduced pressure. The residue was purified by silica gel column chromatography (diluting solvent: chloroform/methanol=4:1), and recrystallized from acetonitrile to give 2.77 g (yield: 71%) of the desired product compound as a brown powder. The melting point was 179.5–181.5° C.

Elemental analysis (as $C_{17}H_{15}NO_3S$): Calcd. (%); C: 65.16, H: 4.82, N: 4.47; Found (%); C: 64.96, H: 4.78, N: 4.83

EXAMPLE 71

2-(5-hexyloxy-1H-indol-2-yl)thio-2-phenylpropionic acid (i) To a solution of 7-hydroxy-2-methyl-2-phenylthiazolo[3,2-a]indol-3(2H)-one (2.86 g), n-hexyl bromide (1.76 g) and a small amount of potassium iodide, and the mixture was heated and refluxed for 33 hours. The reaction mixture was allowed to cool. Then insoluble matter was filtered. The solvent was evaporated off under reduced pressure. Water was added to the residue, and the mixture was extracted with ethyl acetate. The organic layer was washed with water and a saturated aqueous sodium chloride solution, and was dried over anhydrous sodium sulfate. The solvent was evaporated under reduced pressure. The residue was purified by silica gel column chromatography (diluting solvent: n-hexane/ethyl acetate=9:1) to give 3.4 g (yield: 93%) of 7-hexyloxy-2-methyl-2-phenylthiazolo[3,2-a]indol-3-(2H)-one.

(ii) To 7-hexyloxy-2-methyl-2-phenylthiazolo[3,2-a]indol-3(2H)-one (3.92 g), 2N sodium hydroxide (70 ml) was added, and the mixture was heated and refluxed for 1.5 hours. The reaction mixture was allowed to cool, and the deposited crystalline matter was collected by filtration. The crystalline matter was dissolved in methanol. The solution was made acidic by adding concentrated hydrochloric acid under ice cooling, and the solvent was evaporated under reduced pressure. Water was added to the residue, and the mixture was extracted with ethyl acetate. The organic layer was dried over anhydrous sodium sulfate. The solvent was evaporated under reduced pressure, to give 3.81 g (yield: 93 %) of the desired compound as a colorless powder. The melting point was 100°–102° C.

Elemental analysis (as $C_{23}H_{27}NO_3S$) Calcd. (%); C: 69.49, H: 6.85, N: 3.52; Found (%); C: 69.36, H: 6.94, N: 3.71

EXAMPLE 72

Benzyl 2-(1H-indol-2-yl)thio-2-phenylpropionate

To a solution (5 ml) of 2-(1H-indol-2-yl)thio-2-phenylpropionic acid (1.5 g) and diethyl azodicarboxylate (0.96 g) in anhydrous tetrahydrofuran, a solution (5 ml) of benzyl alcohol (0.81 g) and triphenylphoshine (1.44 g) in anhydrous tetrahydrofuran was added dropwise under an argon atmosphere, and the mixture was stirred at room temperature overnight. The solvent was evaporated off under reduced pressure. Benzene was added to the residue, and deposited crystalline matter was filtered and the solvent was evaporated. The residue was purified by silica gel column chromatography (diluting solvent: n-hexane/ethyl acetate=9:1), and was further recrystallized from ethyl acetate/n-hexane to give 1.37 g (yield 71 %) of the product compound as a colorless scale-like crystal. The melting point was 102°–103° C.

Elemental analysis (as $C_{24}H_{21}NO_2S$) Calcd. (%); C: 74.39, H: 5.46, N: 3.61; Found (%); C: 74.46, H: 5.47, N: 3.57

EXAMPLE 73

2-(1-methylindol-2-yl)thio-2-phenylpropanol

A solution (20 ml) of ethyl 2-(1-methylindol-2-yl)thio-2-phenylpropionate (3 g) in anhydrous tetrahydrofuran was added dropwise to a suspension (75 ml) of lithium aluminum hydride (670 mg) in anhydrous tetrahydrofuran, and the mixture was heated and refluxed for 2 hours. The reaction solution was allowed to cool, and was poured into ice water. The mixture was acidified by adding 6N hydrochloric acid, and was extracted with ethyl acetate. The organic layer was washed with water and a saturated aqueous sodium chloride solution, and was dried over anhydrous sodium sulfate. The solvent was evaporated under reduced pressure. The resulting residue was recrystallized from ligroin to give 1.84 g (yield: 70 %) of the product compound as a pale yellow powder. The melting point was 118°–119° C.

Elemental analysis (as $C_{18}H_{19}NOS$) Calcd. (% ; C: 72.69, H: 6.44, N: 4.71; Found (%); C: 72.59, H: 6.50, N: 4.70

EXAMPLES 74 TO 84

The compounds shown in Table 3 were synthesized in a similar manner as in Example 73.

TABLE 3
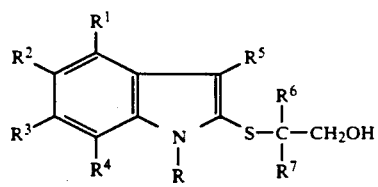
| Example | R | R¹ | R² | R³ | R⁴ | R⁵ | R⁶ | R⁷ | Melting Point (°C.) | Elemental Analysis (%) Calcd. Found C | H | N |
|---|---|---|---|---|---|---|---|---|---|---|---|---|
| 74 | H | H | H | H | H | H | $C_2H_5$ | ⌬ | 89–91 | 72.69 72.54 | 6.44 6.47 | 4.71 4.67 |
| 75 | $CH_3$ | H | H | H | H | H | $C_2H_5$ | ⌬ | 76–79 | 73.27 73.39 | 6.80 6.84 | 4.50 4.49 |
| 76 | H | H | H | H | H | H | n-$C_4H_9$ | H | Oily | 67.43 67.81 | 7.68 7.31 | 5.62 6.42 |
| 77 | H | H | H | H | H | H | n-$C_3H_7$ | ⌬ | 107–108.5 | 73.27 73.28 | 6.80 6.82 | 4.50 4.40 |
| 78 | $CH_3$ | H | H | H | H | H | n-$C_3H_7$ | ⌬ | Oily | 73.81 73.29 | 7.12 7.08 | 4.30 4.51 |
| 79 | H | H | H | H | H | H | $(CH_3)_2CH(CH_2)_2$ | ⌬ | 76–78 | 74.29 73.99 | 7.42 7.35 | 4.13 4.07 |
| 80 | H | H | H | H | OH | H | $CH_3$ | ⌬ | 105–107 | 65.09 65.17 | 6.50 6.54 | 3.61*¹ 3.63 |
| 81 | H | H | H | Cl | H | H | $CH_3$ | ⌬ | 101–102 | 64.24 64.17 | 5.07 5.06 | 4.41 4.35 |
| 82 | H | H | H | H | PhCH₂O | H | $CH_3$ | ⌬ | 113–114.5 | 74.00 73.99 | 5.95 5.97 | 3.60 3.53 |
| Example | R | R⁴ | R¹ | R² | R³ | R⁵ | R⁶ | R⁷ | Melting Point (°C.) | Elemental Analysis (%) Calcd. Found C | H | N |
|---|---|---|---|---|---|---|---|---|---|---|---|---|
| 83 | —CH₂CH₂CH₂— | | H | H | H | H | $CH_3$ | ⌬ | 89–91 | 74.27 74.60 | 6.54 6.57 | 4.33 4.29 |

TABLE 3-continued

[Structure: indole with substituents R¹, R², R³, R⁴ on benzene ring, R⁵ at 3-position, N-R, and at 2-position S–C(R⁶)(R⁷)–CH₂OH]

| 84 | —CH₂CH₂O— | H | H | H | H | CH₃ | (phenyl) | 116 | 70.13<br>70.17 | 5.88<br>5.90 | 4.30<br>4.26 |

*¹Calculated as ethyl acetate

EXAMPLE 85

2-(5-hexyloxy-1H-indol-2-yl)thio-2-phenylpropanol

A solution (20 ml) of 2-(5-hexyloxy-1H-indol-2-yl)thio-2-phenylpropionic acid (2.81 g) in anhydrous tetrahydrofuran was added dropwise to a suspension (10 ml) of lithium aluminum hydride (0.4 g) in anhydrous tetrahydrofuran, and the mixture was heated and refluxed for 30 minutes. The reaction solution was allowed to cool, and was poured into ice water. The mixture was acidified by adding 6N hydrochloric acid, and extracted with ethyl acetate. The organic layer was washed with water, and a saturated aqueous sodium chloride solution, and was dried over anhydrous sodium sulfate. The solvent was evaporated, and the residue was crystallized by adding n-hexane. The crude crystalline matter was recrystallized from ethanol to give 1.66 g (yield: 61 %) of the product compound as a pale green prism crystal. The melting point was 93.5°–95.5° C.

Elemental analysis (as $C_{23}H_{29}NO_2S$): Calcd. (%); C: 72.02, H: 7.62, N: 3.65; Found (%); C: 72.11, H: 7.64, N: 3.65

EXAMPLE 86

2-(5-hydroxy-1H-indol-2-yl)thio-2-phenylpropanol

The product compound was prepared in the same manner as in Example 85 except that 2-(5-hydroxy-1H-indol-2-yl)thio-2-phenylpropionic acid was used as the starting material. The yield was 24.5 %, and the melting point was 143°–145° C.

Elemental analysis (as $C_{17}H_{17}NO_2S$) Calcd. (%); C: 68.20, H: 5.72, N: 4.68; Found (%); C: 67.96, H: 5.70, N: 4.89

EXAMPLE 87

2-(1H-indol-2-yl)thio-2-phenylpropanol

To a solution (20 ml) of 2-(1H-indol-2-yl)thio-2-phenylpropionic acid (5.0 g) in anhydrous tetrahydrofuran triethylamine (1.7 g) was added. Thereafter, a solution (8 ml) of ethyl chloroformate (1.8 g) in anhydrous tetrahydrofuran was added dropwise under argon atmosphere with ice cooling. The mixture was stirred at that temperature for one hour. The deposited salt was filtered off to prepare a solution of a mixed acid anhydride in tetrahydrofuran. This mixed acid anhydride solution was added to a suspension of sodium borohydride (2.2 g) in water (30 ml) within the temperature range of from 10° to 15° C., and the mixture was stirred at that temperature for 4 hours. The reaction solution was acidified by adding concentrated hydrochloric acid, and extracted by ethyl acetate. The organic layer was washed with water, and a saturated aqueous sodium chloride solution, and was dried over anhydrous sodium sulfate. The solvent was evaporated under reduced pressure. The residue was purified by silica gel column chromatography (diluting solvent: methylene chloride), and further recrystallized from acetonitrile to give 2.4 g (yield: 48 %) of the product compound as a colorless powder. The melting point was 125.5°–127° C.

Elemental analysis (as $C_{17}H_{17}NOS$): Calcd. (%); C: 72.05, H: 6.05, N: 4.94; Found (%); C: 71.99, H: 6.25, N: 4.82

EXAMPLE 88

2-(1H-indol-2-yl)thio-2-phenylpropyl acetate

To a solution (20 ml) of 2-(1H-indol-2-yl)thio-2-phenylpropanol (2.81 g) and N,N-dimethylaniline (1.23 g) in anhydrous DMF, was a solution (2 ml) of acetyl chloride (0.86 g) in anhydrous DMF was added dropwise. The mixture was stirred at room temperature overnight. The reaction solution was diluted with water, and was extracted with ethyl acetate. The organic layer was washed with 1N hydrochloric acid, water, and a saturated aqueous sodium chloride solution, and was dried over anhydrous sodium sulfate. The solvent was evaporated off under reduced pressure. The residue was purified by silica gel column chromatography (diluting solvent: n-hexane/ethyl acetate =9:1), and further recrystallized from ethanol to give 1.35 g (yield: 42 %) of the product compound as a pale yellow prism crystal. The melting point was 105°–106° C.

Elemental analysis (as $C_{19}H_{19}NO_2S$): Calcd. (%); C: 70.12, H: 5.89, N: 4.30; Found (%); C: 70.01, H: 5.88, N: 4.28

EXAMPLE 89

2-(1-methylindol-2-yl)thio-2-phenylpropyl crotonate

To a solution (30 ml) of 2-1-methylindol-2-yl)thio-2-phenylpropanol (3 g) and triethylamine (1.4 ml) in anhydrous dioxane, a solution (5 ml) of crotonyl chloride (0.97 ml) in anhydrous dioxane was added dropwise at 0° C. The reaction solution was stirred at room temperature for 3.5 hours, and deposited salt was filtered off. The filtrate was poured into water, and extracted with ethyl acetate. The organic layer was washed with water, and a saturated sodium chloride solution, and was dried over anhydrous sodium sulfate. The solvent was evaporated under reduced pressure. The residue was crystallized by adding n-hexane, and was further recrystallized from n-hexane to give 2.56 g (yield: 69 %) of the product compound as a colorless powder. The melting point was 56°-57° C.

Elemental analysis (as $C_{22}H_{23}NO_2S$): Calcd. (%); C: 72.30, H: 6.34, N: 3.83; Found (%); C: 72.24, H: 6.32, N: 3.88

EXAMPLE 90

2-(1-methylindol-2-yl)thio-2-phenylpentyl crotonate

The product compound was obtained (yield: 82 %) as a pale yellow oil in the same manner as in Example 87 but using 2-(1-methylindol-2-yl)thio-2-phenylpentanol as a starting material.

Elemental analysis (as $C_{24}H_{27}NO_2S$): Calcd. (%); : 73.24, H: 6.92, N: 3.56; Found (%); C: 73.18, H: 6.90, N: 3.31

EXAMPLE 91

2-(1-methylindol-2-yl)thio-2-phenylpropyl 2-butenyl ether

60 % sodium hydride (0.37 g) was washed with n-pentane. Anhydrous DMF (35 ml) was added thereto. To the resulting suspension, a solution (15 ml) of 2-(1-methylindol-2-yl)thio-2-phenylpropanol (2.5 g) in anhydrous DMF was added dropwise at room temperature, and the mixture was stirred at the same temperature for 30 minutes. To this reaction mixture, a solution (5 ml) of crotyl bromide (0.9 ml) in anhydrous DMF was added dropwise at 0° C., and stirred at the same temperature for 10 minutes, at room temperature for 2 hours, and further at 70°-80° C. for 30 minutes. The reaction mixture was allowed to cool, poured into ice water, and extracted with ether. The organic layer was washed with water, and a saturated aqueous sodium chloride solution, and was dried over anhydrous sodium sulfate. The solvent was evaporated. The residue was purified by silica gel column chromatography (diluting solvent: n-hexane/ethyl acetate=10:1) to give 1.5 g (yield: 51 %) of the product compound as a pale yellow oil.

Mass (m/e): 351(M+)

NMR (CDCl$_3$)δ: 1.52-1.71 (3H,m), 1.73 (3H,s), 3.33 (3H,s), 3.77-3.95 (4H,m), 5.50-5.63 (2H,m), 6.64 (1H,s), 7.02-7.62 (9H,m)

EXAMPLE 92

Methyl 2-(1-methylindol-2-yl)thio-2-phenylbutyrate

60 % sodium hydride (0.89 g) was washed with n-pentane, and thereto anhydrous DMF (80 ml) was added. To the suspension, a solution (20 ml) of methyl 2-(1H-indol-yl)thio-2-phenylbutyrate (6.87 g) in anhydrous DMF was added dropwise at room temperature. The mixture was stirred at that temperature for 20 minutes. To this reaction mixture, a solution (5 ml) of methyl iodide (1.45 ml) in anhydrous DMF was added dropwise under ice cooling, and the mixture was stirred at room temperature for 2.5 hours. The reaction mixture was poured into ice water, and was extracted with ether. The organic layer was washed with water, and a saturated aqueous sodium chloride solution, and was then dried over anhydrous sodium sulfate. The solvent was evaporated. The residue was purified by silica gel column chromatography (diluting solvent: benzene/n-hexane=3:1), and further recrystallized to give 4.89 g (yield 68 %) of the title compound as pale yellow prisms. The melting point was 90°-91° C.

Elemental analysis (as $C_{20}H_{21}NO_2S$): Calcd. (%); C: 70.77, H: 6.24, N: 4.13; Found (%); C: 70.77, H: 6.24, N: 4.11

EXAMPLE 93

Ethyl 2-(1-ethoxycarbonylmethylindol-2-yl)thio-2-phenylpropionate

Starting from ethyl 2-(1H-indol-2-yl)thio-2-phenylpropionate and ethyl bromoacetate, the title compound was obtained as a pale yellow oily matter (yield: 63 %) according to the method of Example 92.

The usefulness of the compounds of the present invention is shown by the following experiments.

EXPERIMENT 1

Effect On Serum Lipid of Normal Rat

The compound of the present invention, which is suspended in 0.5 % carboxymethylcellulose (CMC) solution, was given orally to Wistar strain male rats weighing from 200 to 250 g with one dose per day for 4 days. Thereafter, the serum lipid level was measured, and compared with the level of the normal rat. Table 4 shows the result in terms of the ratio (%) to the normal rat.

TABLE 4

| Example | Dose (mg/kg) | TCh | LDL-Ch | AI |
|---|---|---|---|---|
| 1 | 100 | 61.5** | 17.8 | 21.1 |
| 39 | 3.125 | 75.6** | 29.9** | 31.7* |
|  | 6.25 | 84.8* | 66.0 | 70.7 |
|  | 12.5 | 74.3* | 52.8 | 58.5 |
|  | 25 | 44.4*** | 9.1** | 14.6** |
| 40 | 100 | 42.6** | 13.6** | 22.4* |
| 48 | 100 | 56.5** | 24.3 | 34.2 |
| 52 | 100 | 22.7*** | 8.6 | 42.1 |
| 74 | 3.125 | 86.5** | 75.5* | 82.8 |
|  | 6.25 | 92.4 | 81.5 | 81.7 |
|  | 12.5 | 80.9*** | 58.3** | 60.2* |
|  | 25 | 68.9*** | 40.1*** | 41.9** |
|  | 50 | 62.1** | 19.5*** | 18.3*** |
| 75 | 100 | 63.4* | 32.4* | 34.9* |
| 86 | 25 | 66.0* | 34.8* | 42.0* |
| 87 | 3.125 | 80.7* | 49.7 | 53.7 |
|  | 6.25 | 74.5** | 41.6* | 46.3 |
|  | 12.5 | 63.4*** | 29.9** | 39.0* |
|  | 25 | 51.5*** | 14.7*** | 19.5*** |
|  | 50 | 26.7*** | 3.6** | 12.2** |
| 88 | 25 | 65.3*** | 32.8*** | 37.6*** |

The numerals show the percentages of the measured level relative to the level of the normal group.
Each group consisted of 5 rats.
*$P < 0.05$
**$P < 0.01$
***$P < 0.001$, significantly different from the level of the control group.
TCh: Total cholesterol
LDL-Ch: Low density lipoprotein cholesterol
AI: Arteriosclerotic index (LDL-Ch/HDL-Ch)

EXPERIMENT 2

Effect on serum lipid of rats fed with high cholesterol diet

Wistar strain male rats weighing from 200 to 250 g were fed with a high cholesterol diet containing 1 % cholesterol, 0.2 % cholic acid, and 2.5 % olive oil, and were dosed orally with a compound of the present invention which is suspended in a 0.5 % CMC solution, with one dose per day for 5 days. Thereafter, the level of the serum lipid was measured. The results are shown in Table 5 in terms of inhibition rate in comparison with the level of the control group which were fed with the high cholesterol diet and dosed with a CMC solution.

TABLE 5

Inhibition of Rise of Serum Lipid Level in Rats Fed with High Cholesterol Diet

| Example | Dose (mg/kg) | TCh | HDL-Ch | LDL-Ch | AI |
|---|---|---|---|---|---|
| 39 | 12.5 | 55.8* | 85.7* | 57.7* | 68.2* |
|  | 25 | 94.8** | 144.8** | 98.0** | 98.7** |
|  | 50 | 105.5** | 146.4 | 108.2** | 106.4** |
| 74 | 12.5 | 32.7* | 38.7 | 33.2* | 43.1* |
|  | 25 | 53.6** | 42.3* | 52.7** | 59.5** |
|  | 50 | 69.7** | 108.1 | 72.8** | 71.2* |
| 87 | 12.5 | 62.7* | 118.8 | 66.3* | 70.1* |
|  | 25 | 105.7** | 150.9** | 108.6** | 106.4** |
|  | 50 | 111.3*** | 74.1 | 108.9** | 106.9** |

The numerals show the rate of inhibition of the rise (rate of inhibition of the fall in the case of the HDL-Ch).

$$\text{Inhibition rate (\%)} = \frac{(\text{Level of control group} - \text{Level of compound-dosed group})}{(\text{Level of control group} - \text{Level of normal group})} \times 100$$

The one group consisted of 5 rats.
*P < 0.05
**P < 0.01
***P < 0.001, significantly different from the level of the control group.
TCh: Total cholesterol
HDL-Ch: High density lipoprotein cholesterol
LDL-CH: Low density lipoprotein cholesterol
AI: Arteriosclerotic index (LDL-Ch/HDL-Ch)

The above results show that the compounds of the present invention lower the total cholesterol level and the arteriosclerotic low-density-lipoprotein-cholesterol level or inhibit it's rise, and simultaneously ameliorate the arteriosclerotic index.

The acute toxicity of the compounds of Example 38 and Example 85 to ICR strain mice was studied. The oral doses of 1 g/kg, and 3 g/kg, respectively, did not cause any abnormality nor death of any mouse, which proves the low toxicity of the compounds of the present invention.

What is claimed is:
1. A compound selected from the group consisting of:
Ethyl 2-(1H-indol-2-yl)thio-2-phenylpropionate;
2-(1H-indol-2-yl)thio-2-phenylpropionic acid;
2-(5-hydroxy-1H-indol-2-yl)thio-2-phenylpropionic acid;
2-(5-hexyloxy-1H-indol-2-yl)thio-2-phenylpropionic acid;
Benzyl 2-(1H-indol-2-yl)thio-2-phenylpropionate;
2-(1-methylindol-2-yl)thio-2-phenylpropanol;
2-(5-hexyloxy-1H-indol-2-yl)thio-2-phenylpropanol;
2-(1H-indol-2-yl)thio-2-phenylpropanol;
2-(1H-indol-2-yl)thio-2-phenylpropyl acetate;
2-(1-methylindol-2-yl)thio-2-phenylpropyl crotonate;
2-(1-methylindol-2-yl)thio-2-phenylpentyl crotonate;
2-(1-methylindol-2-yl)thio-2-phenylpropyl 2-butenyl ether;
Methyl 2-(1-methylindol-2-yl)thio-2-phenylbutyrate;
Ethyl 2-(1-ethoxycarbonylmethylindol-2-yl)thio-2-phenylpropionate;
2-(1-methylindol-2-yl)thio-2-phenylpropionic acid;
2-(1H-indol-2-yl)thio-2-phenylbutanoic acid;
2-(5-methyl-1H-indol-2-yl)thio-2-phenylpropionic acid;
2-(1H-indol-2-yl)thio-2-phenylbutanol;
2-(1-methylindol-2-yl)thio-2-phenylbutanol; and
2-(3-methyl-1H-indol-2-yl)-(thio-2-phenylpropionic acid).

2. A composition comprising a pharmaceutically acceptable carrier an anti-hyperlipidemia effective amount of a compound selected from the group consisting of:
Ethyl 2-(1H-indol-2-yl)thio-2-phenylpropionate;
2-(1H-indol-2-yl)thio-2-phenylpropionic acid;
2-(5-hydroxy-1H-indol-32-yl)thio-2-phenylpropionic acid;
2-(5-hexyloxy-1H-indol-2-yl)thio-2-phenylpropionic acid;
Benzyl 2-(1H-indol-2-yl)thio-2-phenylpropionate;
2-(1-methylindol-2-yl)thio-2-phenylpropanol;
2-(5-hexyloxy-1H-indol-b 2-yl)thio-2-phenylpropanol;
2-(1H-indol-2-yl)thio-2-phenylpropanol;
2-(1H-indol-2-yl)thio-2-phenylpropyl acetate;
2-(1-methylindol-2-yl)thio-2-phenylpropyl crotonate;
2-(1-methylindol-2-yl)thio-2-phenylpentyl crotonate;
2-(1-methylindol-2-yl)thio-2-phenylpropyl 2-butenyl ether;
Methyl 2-(1-methylindol-2-yl)thio-2-phenylbutyrate;
Ethyl 2-(1-ethoxycarbonylmethylindol-2-yl)thio-2-phenylpropionate;
2-(1-methylindol-2-yl)thio-2-phenylpropionic acid;
2-(1H-indol-2-yl)thio-2-phenylbutanoic acid;
2-(5-methyl-1H-indol-2-yl)thio-2-phenylpropionic acid;
2-(1H-indol-2-yl)thio-2-phenylbutanol;
2-(1-methylindol-2-yl)thio-2-phenylbutanol, and
2-(methyl-1H-indol-2yl)-(thio-2-phenylpropionic acid).

* * * * *